United States Patent
Muruganantham

(10) Patent No.: US 9,528,418 B2
(45) Date of Patent: Dec. 27, 2016

(54) SINGLE SENSOR MONITORING SYSTEM FOR MULTIPLE AFTER-TREATMENT SYSTEMS ON ENGINES

(71) Applicant: Cummins Emission Solutions, Inc., Columbus, IN (US)

(72) Inventor: Karthik Muruganantham, Stoughton, WI (US)

(73) Assignee: CUMMINS EMISSION SOLUTIONS, INC., Columbus, IN (US)

(*) Notice: Subject to any disclaimer, the term of this patent is extended or adjusted under 35 U.S.C. 154(b) by 0 days.

(21) Appl. No.: 14/597,849

(22) Filed: Jan. 15, 2015

(65) Prior Publication Data
US 2016/0208669 A1    Jul. 21, 2016

(51) Int. Cl.
| | |
|---|---|
| *F01N 3/00* | (2006.01) |
| *F01N 3/10* | (2006.01) |
| *F01N 9/00* | (2006.01) |
| *G01N 33/00* | (2006.01) |
| *F01N 11/00* | (2006.01) |

(52) U.S. Cl.
CPC ............... *F01N 9/00* (2013.01); *F01N 11/007* (2013.01); *G01N 33/0037* (2013.01)

(58) Field of Classification Search
CPC ...... F01N 13/04; F01N 3/2066; F01N 3/0842; F01N 3/103; F01N 9/00; F01N 11/007; G01N 33/0037
USPC ............................ 60/276, 287, 288, 301, 311
See application file for complete search history.

(56) References Cited

U.S. PATENT DOCUMENTS

| | | | | |
|---|---|---|---|---|
| 7,640,728 | B2* | 1/2010 | Yoshizaki | B01D 53/9431 60/286 |
| 7,665,297 | B2* | 2/2010 | Suzuki | F01N 3/0821 123/198 F |
| 2010/0313550 | A1 | 12/2010 | Kopp et al. | |
| 2010/0319320 | A1 | 12/2010 | Mital et al. | |
| 2012/0210697 | A1* | 8/2012 | Garimella | F01N 3/208 60/274 |

FOREIGN PATENT DOCUMENTS

WO    WO-2012/051273    4/2012

OTHER PUBLICATIONS

Search Report Issued for United Kingdom Patent Application No. GB 1600621.5, issued on Aug. 5, 2016, 3 pages.

* cited by examiner

*Primary Examiner* — Thomas Denion
*Assistant Examiner* — Diem Tran
(74) *Attorney, Agent, or Firm* — Foley & Lardner LLP

(57) ABSTRACT

An aftertreatment system comprises a first passageway to receive a first portion and a second passageway to receive a second portion of the exhaust gas from the engine. The first and second passageways can have the same length. A first selective catalytic reduction system is fluidly coupled to the first passageway to receive and treat the first portion. A second selective catalytic reduction system is fluidly coupled to the second passageway to receive and treat the second portion. A plurality of sensors are disposed on the first passageway and/or the first selective catalytic reduction system to sense operational parameters of the first portion of the exhaust gas. A controller is in electronic communication with the plurality of sensors to determine the operational parameters of the first portion and to determine operational parameters of the second portion of the exhaust gas based upon the first operational parameters.

25 Claims, 3 Drawing Sheets

SINGLE SENSOR MONITORING SYSTEM FOR MULTIPLE AFTER-TREATMENT SYSTEMS ON ENGINES

TECHNICAL FIELD

The present disclosure relates generally to aftertreatment systems for use with internal combustion (IC) engines.

BACKGROUND

Exhaust aftertreatment systems are used to receive and treat exhaust gas generated by IC engines. Conventional exhaust gas aftertreatment systems include any of several different components to reduce the levels of harmful exhaust emissions present in exhaust gas. For example, certain exhaust aftertreatment systems for diesel-powered IC engines include a selective catalytic reduction (SCR) catalyst to convert NOx (NO and $NO_2$ in some fraction) into harmless nitrogen gas ($N_2$) and water vapor ($H_2O$) in the presence of ammonia ($NH_3$).

Generally in such conventional aftertreatment systems, an exhaust reductant (e.g., a diesel exhaust fluid such as urea) is injected into the aftertreatment system to provide a source of ammonia, and mixed with the exhaust gas to partially reduce the NOx gases. The reduction byproducts of the exhaust gas are then fluidically communicated to a catalyst included in the SCR aftertreatment system to decompose substantially all of the NOx gases into relatively harmless byproducts which are expelled out of such conventional SCR aftertreatment systems.

Engines that use aftertreatment systems for treating the exhaust gas (e.g., diesel exhaust gas) can include bigger engines used in several off-highway applications. These applications include engines that have a volumetric capacity of greater than about 15 liters, which are typically used in on-road trucks. Due to the large amount of exhaust gas emitted by bigger engines, such engines often include aftertreatment systems that include a plurality of SCR systems (e.g., 2, 3, 4 or even more) for treating the exhaust gas. The exhaust gas is generally divided into equal portions such that each portion flows through a single SCR system disposed on a separate fluidic pathway and configured to treat only the portion of the exhaust gas that flows through that SCR system. Sensors for sensing temperature, NOx gases, ammonia, oxygen, etc. are disposed on each aftertreatment system and provide information on operational parameters of each portion of the exhaust gas. This increases the overall size of the aftertreatment systems and increases cost.

SUMMARY

Embodiments described herein relate generally to aftertreatment systems for use with engines. Embodiments described herein particularly relate to aftertreatment systems for use with off-highway engines that include a plurality of SCR systems, and include operational parameter sensors disposed on only a single SCR system of the plurality of SCR systems.

In some embodiments, an aftertreatment system comprises a first passageway configured to receive a first portion of an exhaust gas from an engine. A second passageway is configured to receive a second portion of the exhaust gas from the engine. A first selective catalytic reduction system is fluidly coupled to the first passageway. The first selective catalytic reduction system is configured to receive the first portion of the exhaust gas, and treat the first portion of the exhaust gas. A second selective catalytic reduction system is fluidly coupled to the second passageway. The second selective catalytic reduction system is configured to receive the second portion of the exhaust gas and treat the second portion of the exhaust gas.

A plurality of sensors are disposed on at least one of the first passageway and the first selective catalytic reduction system. The plurality of sensors are configured to sense operational parameters of the first portion of the exhaust gas. A controller is in electronic communication with the plurality of sensors. The controller is configured to determine the operational parameters of the first portion of the exhaust gas based upon signals received from the plurality of sensors. The controller is also configured to determine operational parameters of the second portion of the exhaust gas based upon the first operational parameters.

In one embodiment, the first passageway has a first length and the second passageway has a second length which is about the same as the first length. In another embodiment, the first passageway has a first length and the second passageway has a second length which is different from the first length. In such embodiments, the controller is also configured to determine a correction factor from the first length and the second length. The controller then uses the correction factor to determine the operational parameters of the second portion from the operational parameters of the first portion.

In other embodiments, a monitoring system for determining operational parameters of an exhaust gas flowing through an aftertreatment system comprises a plurality of sensors disposed on at least one of a first passageway and a first selective catalytic reduction system. The first passageway is configured to receive a first portion of the exhaust gas from an engine. The first selective catalytic reduction system is fluidly coupled to the first passageway. The first selective catalytic reduction system is configured to receive the first portion of the exhaust gas and treat the first portion of the exhaust gas. The plurality of sensors are configured to sense operational parameters of the first portion of the exhaust gas.

A controller is in electronic communication with the plurality of sensors, the controller is configured to receive electronic signals from the plurality of sensors and determine the operational parameters of the first portion of the exhaust gas. The controller is further configured to determine operational parameters of a second portion of the exhaust gas from the first operational parameters. The second portion of the exhaust gas flows through a second passageway and a second selective catalytic reduction system. The second passageway is configured to receive the second portion of the exhaust gas from the engine. The second selective catalytic reduction system is fluidly coupled to the second passageway. The second selective catalytic reduction system is configured to receive the second portion of the exhaust gas and treat the second portion of the exhaust gas. In one embodiment, the first passageway has a first length and the second passageway has a second length which about the same as the first length. In another embodiment, the first length is the same as the second length.

In still other embodiments, a controller module for determining operational parameters of an exhaust gas comprises a receiving module configured to receive signals from a plurality of sensors disposed on at least one of a first passageway and a first selective catalytic reduction system. The first passageway is configured to receive a first portion of the exhaust gas from an engine. The first selective catalytic reduction system is fluidly coupled to the first passageway. The first selective catalytic reduction system is configured to receive the first portion of the exhaust gas and treat the first portion of the exhaust gas. The plurality of sensors are configured to sense operational parameters of the first portion of the exhaust gas.

A first determination module is configured to process the signals to determine the operational parameters of the first portion of the exhaust gas. A second determination module is configured to determine operational parameters of a second portion of the exhaust gas from the first operational parameters. The second portion of the exhaust gas flows through a second passageway and a second selective catalytic reduction system. The second passageway is configured to receive the second portion of the exhaust gas from the engine. The second selective catalytic reduction system is fluidly coupled to the second passageway. The second selective catalyst reduction system is configured to receive the second portion of the exhaust gas and treat the second portion of the exhaust gas. In one embodiment, the first passageway has a first length and the second passageway has a second length about the same as the first length. In other embodiments, the first length is different from the second length.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein.

BRIEF DESCRIPTION OF DRAWINGS

The foregoing and other features of the present disclosure will become more fully apparent from the following description and appended claims, taken in conjunction with the accompanying drawings. Understanding that these drawings depict only several implementations in accordance with the disclosure and are therefore, not to be considered limiting of its scope, the disclosure will be described with additional specificity and detail through use of the accompanying drawings.

Figure 1:
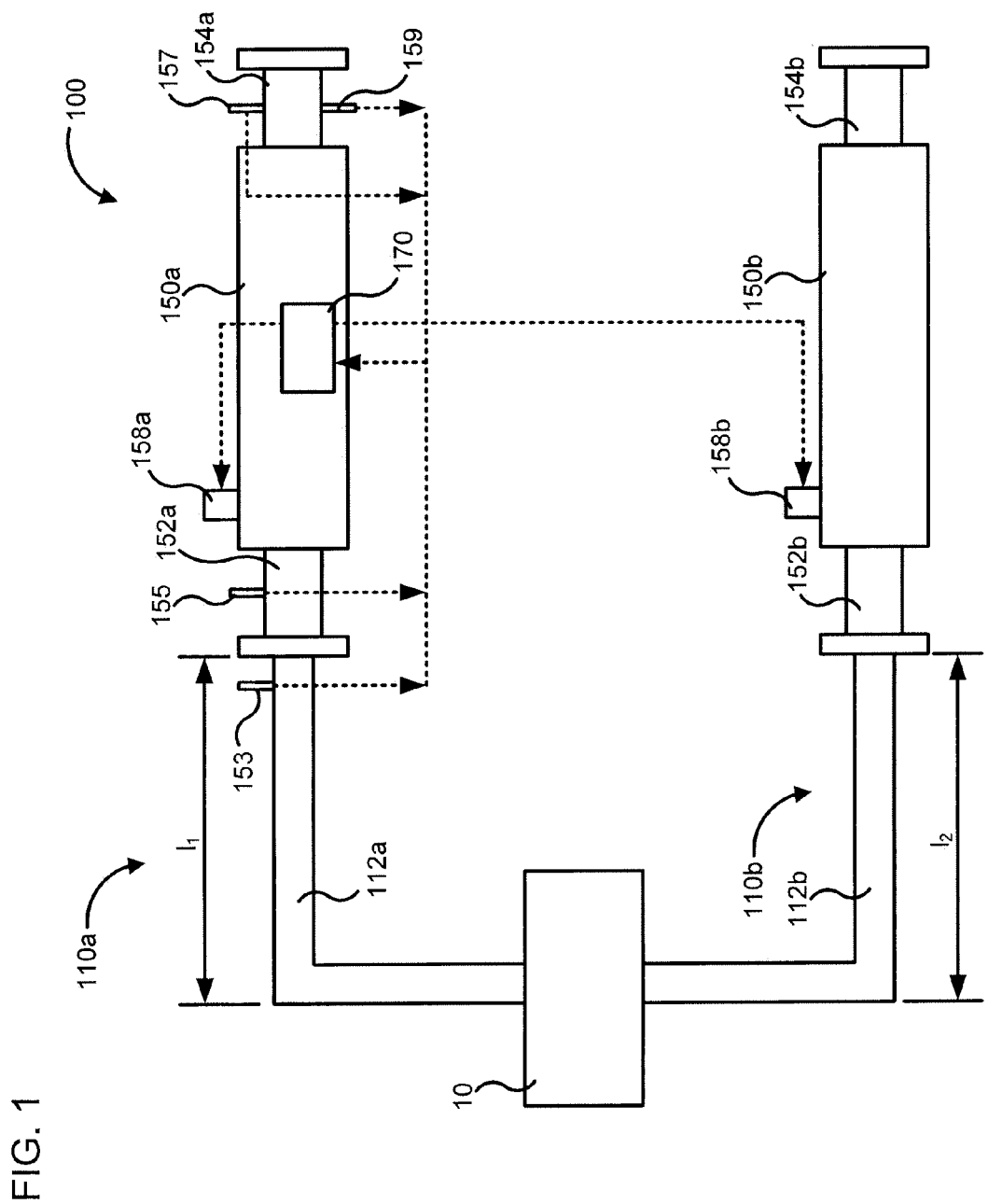
FIG. 1 is a schematic diagram of an embodiment of an aftertreatment system that includes a first bank having a first passageway, a first selective catalytic reduction system, a second bank having a second passageway and a second selective catalytic reduction system, and a plurality of sensors disposed only on the first bank.

Reference is made to the accompanying drawings throughout the following detailed description. In the drawings, similar symbols typically identify similar components, unless context dictates otherwise. The illustrative implementations described in the detailed description, drawings, and claims are not meant to be limiting. Other implementations may be utilized, and other changes may be made, without departing from the spirit or scope of the subject matter presented here. It will be readily understood that the aspects of the present disclosure, as generally described herein, and illustrated in the figures, can be arranged, substituted, combined, and designed in a wide variety of different configurations, all of which are explicitly contemplated and made part of this disclosure.

DETAILED DESCRIPTION OF VARIOUS EMBODIMENTS

Embodiments described herein relate generally to aftertreatment systems for use with engines. Embodiments described herein particularly relate to aftertreatment systems for use with off-highway engines that include a plurality of SCR systems, and include operational parameter sensors disposed on only a single SCR system of the plurality of SCR systems.

Embodiments described herein may provide a number of benefits including, for example: (1) disposing sensors on a on only one passageway and/or SCR system included in an aftertreatment system that includes a plurality of passageways and SCR systems; (2) determining operational parameters of a plurality of portions of an exhaust gas flowing through the plurality of passageways and SCR systems of the aftertreatment system by measuring the operational parameters of only one portion of the exhaust gas; (3) reducing number of sensors and space required for sensor and associated system; and (4) reducing the overall cost of the aftertreatment system.

FIG. 1 is a schematic diagram of an aftertreatment system 100 for treating an exhaust gas (e.g., a diesel exhaust gas) produced by an engine 10. The aftertreatment system 100 includes a first bank 110a structured to receive a first portion of the exhaust gas, and a second bank 110b structured to receive a second portion of the exhaust gas. The first bank 110a includes a first passageway 112a, a first SCR system 150a and a controller 170. The second bank 110b includes a second passageway 112b and a second SCR system 150b.

The engine 10 can comprise an IC engine, for example, a diesel engine, a gasoline engine, a natural gas engine, a positive displacement engine, a rotary engine, or any other suitable engine, which converts a fossil fuel into mechanical energy. Moreover, the engine 10 can include an off-highway engine, for example, an engine having a volumetric capacity of greater than about 15 liters.

The first passageway 112a is configured to receive the first portion of the exhaust gas from the engine 10. The first passageway 112a can be formed from any suitable material, for example, metals, alloys, ceramics, plastics, any other suitable material or a combination thereof. The first passageway 112a can have any suitable cross-section, for example, circular, rectangular, square, elliptical, or any other suitable cross-section. The first passageway 112a defines a first length $l_1$.

The second passageway 112b is configured to receive the second portion of the exhaust gas form the engine 10. The second passageway 112b can be formed from the same material and have the same cross-section as the first passageway 112a. Furthermore, the second passageway 112b defines a second length $l_2$ which is about the same as the first length $l_1$ of the first passageway 112a. As used herein, "about the same" should be considered to be within +/−5% of each other, i.e. second length $l_2$ is within +/−5% of the first length $l_1$. In particular embodiments, the second length $l_2$ is the same or otherwise equal to the first length $l_1$.

Furthermore, a flow rate of the first portion of the exhaust gas can be similar to a flow rate of the second portion of the exhaust gas. For example, the exhaust gas generated by the engine can be divided equally into the first portion and the second portion. Since the first passageway 112a and the second passageway 112b are about the same length, the first portion and the second portion of the exhaust gas can also have about the same or otherwise equal flow rates as they enters the first SCR system 150a and the second SCR system 150b, respectively.

The first SCR system 150a is fluidly coupled to the first passageway 112a. The first SCR system 150a is configured to receive the first portion of the exhaust gas and treat the first portion of the exhaust gas. The first SCR system 150a includes one or more catalysts formulated to selectively reduce the exhaust gas. Any suitable catalyst can be used such as, for example, platinum, palladium, rhodium, cerium, iron, manganese, copper, and/or vanadium-based catalyst, any other suitable catalyst, or a combination thereof. The catalyst can be disposed on a suitable substrate such as, for example, a ceramic (e.g., cordierite) or metallic (e.g., kanthal) monolith core which can, for example, define a honeycomb structure. A washcoat can also be used as a carrier material for the catalysts. Such washcoat materials can include, for example, aluminum oxide, titanium dioxide, silicon dioxide, any other suitable washcoat material, or a combination thereof. The exhaust gas (e.g., diesel exhaust gas) can flow over and about the catalyst such that any NOx gases included in the exhaust gas are further reduced to yield an exhaust gas which is substantially free of carbon monoxide, and NOx gases.

An injection port 158a is disposed on a sidewall of the first SCR system 150a. The injection port 158a is configured to communicate an exhaust reductant into the first SCR system 150a. In some embodiments, the exhaust gas can include a diesel exhaust gas and the exhaust reductant can include a diesel exhaust fluid. The diesel exhaust fluid may comprise urea, an aqueous solution of urea, or any other fluid that includes ammonia, by products, or any other diesel exhaust fluid as is known in the arts (e.g., the diesel exhaust fluid marketed under the name ADBLUE®).

In particular embodiments, a particulate filter (not shown) can also be disposed upstream of the first SCR system 150a. The filter can comprise any suitable filter (e.g., a diesel particulate filter) configured to filter and remove any particulates entrained within the exhaust gas flow, and prevent such particulates from entering the first SCR system 150a. Such particles can include, for example, dust, soot, organic particles, crystals, or any other solid particulates present in the exhaust gas. In other embodiments, an oxidation catalyst (e.g., a diesel oxidation catalyst) can be included in the aftertreatment system 100 in place of or in combination with the filter. In a particular embodiment, the aftertreatment system can include a diesel oxidation catalyst. The diesel oxidation catalyst can be disposed upstream of the SCR system 150a, for example, in the first passageway 112a or in a housing of the SCR system 150a, or downstream of the SCR system 150a.

In yet another embodiment, a decomposition reactor pipe (not shown) can also be disposed upstream of the first SCR system 150a. The body mixer can be structured to allow efficient mixing of the exhaust reductant with the exhaust gas before communicating the exhaust gas into the first SCR system 150a. The decomposition reactor pipe can include any suitable structures such as, for example, passageways, bluffs, vanes, partition walls, or any other features or structures to facilitate the mixing of the exhaust reductant with the exhaust gas.

The second SCR system 150b is fluidly coupled to the second passageway 112b. The second SCR system 150b is configured to receive the second portion of the exhaust gas and treat the second portion of the exhaust gas. The second SCR system 150b can be substantially similar in structure and function to the first SCR system 150a. The second SCR system 150b also includes an injection port 158b disposed on a sidewall of the second SCR system 150b. The injection port 158b is configured to communicate an exhaust reductant into the second SCR system 150b, as described with respect to the first SCR system 150a. Moreover, a filter, a body mixer and/or an oxidation catalyst can be fluidly coupled to the second SCR system 150b as described with respect to the first SCR system 150a.

Figure 2:
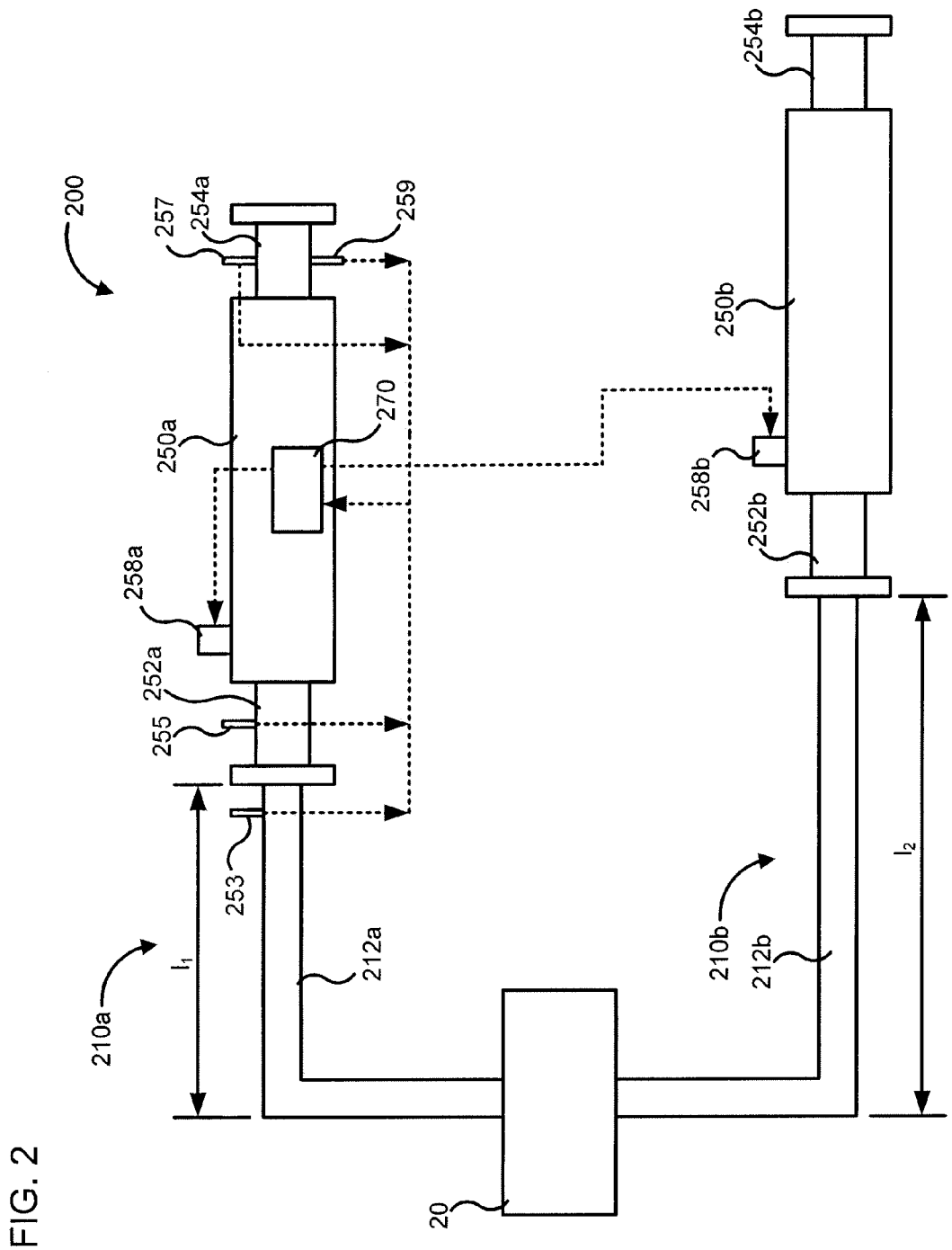
FIG. 2 is a schematic diagram of another embodiment of an aftertreatment system that includes a first bank including a first passageway having a first length, a first selective catalytic reduction system, a second bank including a second passageway having a second length different than the first length, a second catalytic reduction system, and a plurality of sensors disposed only on the first bank.

A plurality of sensors are disposed on the first bank 110a of the aftertreatment system 100, and are configured to sense operational parameters of the first portion of the exhaust gas. As shown in FIG. 2, the plurality of sensors include a first NOx sensor 153 disposed on the first passageway 112a proximal to an inlet 152a of the first SCR system 150a. The first NOx sensor 153 is configured to sense a quantity of NOx in the first portion of the exhaust gas before entering the SCR system 150a. A first temperature sensor 155 is disposed on the inlet 152a and configured to sense a temperature of the first portion of the exhaust gas entering the first SCR system 150a.

A second NOx sensor 157 is disposed on an outlet 154a of the first SCR system 150a and configured to sense a quantity of NOx within the first portion of the exhaust gas exiting the first SCR system 150a. Furthermore, a second temperature sensor 159 is also disposed on the outlet 154a and configured to sense a temperature of the first portion of the exhaust gas exiting the first SCR system 150a. Any other sensors can also be disposed on the first passageway 112a and/or the first SCR system 150a. Such sensors can include, for example, ammonia sensors, and/or oxygen sensors. Moreover, the number of NOx sensors and temperature sensors disposed on the first passageway 112a and/or the first SCR system 150a can also be increased.

The controller 170 is in electronic communication with each of the plurality of sensors (as shown by the dotted arrows in FIG. 2). Furthermore, the controller 170 is also in communication with the first injection port 158a of the first SCR system 150a, and the second injection port 158b for the second SCR system 150b. For example, the controller 170 can be configured to sense and/or or monitor a quantity of the exhaust reductant (e.g., diesel exhaust fluid) communicated into the first SCR system 150a and the second SCR system 150b. The controller 170 can include a processor (e.g., a microprocessor, a programmable logic circuit (PLC) chip, an ASIC chip, or any other processor) capable of executing instructions stored on a computer readable medium (e.g., a random access memory (RAM), a read only memory (ROM), a solid state drive, a flash drive, a hard drive, etc.).

As shown in FIG. 1, the controller 170 is disposed on the first SCR system 150a. In other embodiments, the controller 170 can be disposed at any other location, for example, on the engine 10. In still other embodiments, the controller 170 can be included in an onboard computer, for example, a master controller of a high horse power vehicle (e.g., a truck, a bus, an excavation equipment, etc.) that includes the engine 10.

The controller 170 is configured to determine operational parameters of the first portion of the exhaust gas (e.g., NOx quantity and/or temperature before entering and after exiting the first SCR system 150a). The controller 170 is also configured to determine operational parameters of the second portion of the exhaust gas based upon the operational parameters of the first portion of the exhaust gas. As described herein the first passageway 112a and the second passageway 112b are about the same length, and the first portion and the second portion of the exhaust gas have about the same flow rate. Thus, one or more operational parameters of the first portion and the second portion of the exhaust gas entering and/or exiting the first SCR system 150a and the second SCR system 150b are also about the same.

For example, the amount of NOx gas measured by the first NOx sensor 153 is representative of the expected amount of NOx gas in the second portion of the exhaust gas before entering an inlet 152b of the second SCR system 150b. Similarly, the amount of NOx gas measured by the second NOx sensor 157 is representative of the amount of NOx gas in the second portion of the exhaust gas exiting the second SCR system 150b. Moreover, the temperature of the first portion of the exhaust gas measured at the inlet 152a and the outlet 154a of the first SCR system 150a respectively is representative of the temperature of the second portion of the exhaust gas at the inlet 152b and an outlet 154b of the second SCR system 150b.

In this manner, the controller 170 can determine the operational parameter of each of the first portion and the second portion of the exhaust gas, by only measuring the operational parameters of the first portion of the exhaust gas. In some embodiments, the aftertreatment system 100 can include more than two banks, for example, 3, 4, or even more. In such embodiments, each bank of the aftertreatment system can have its own SCR system. The plurality of sensors can be disposed on only the first bank 110a of the aftertreatment system 100 and configured to measure the operational parameters of the portion of the exhaust gas flowing through the first bank 110a, as described herein. The controller 170 can then determine the operational parameters of the other portions of the exhaust gas flowing through each of the other banks based upon the operational parameters of the first bank 110a.

In a particular embodiment, the aftertreatment system 100 can also include a third bank and a fourth bank. The third bank includes a third passageway and a third SCR system, and the fourth bank includes a fourth passageway and a fourth SCR system. The third passageway is configured to receive a third portion of the exhaust gas from the engine 10. The fourth passageway is configured to receive a fourth portion of the exhaust gas from the engine 10, such that the third portion and the fourth portion of the exhaust gas have about the same flow rate as the flow rate of the first portion of the exhaust gas. Furthermore, the third passageway and the fourth passageway can have lengths or otherwise dimension which are the same as the first length $l_1$ or otherwise dimensions of the first SCR system 150a.

The third SCR system is fluidly coupled to the third passageway. The third SCR system is configured to receive the third portion of the exhaust gas and treat the third portion of the exhaust gas. The fourth SCR system is fluidly coupled to the fourth passageway. The fourth passageway is configured to receive the fourth portion of the exhaust gas and treat the fourth portion of the exhaust gas. Each of the third SCR system and the fourth SCR system can be substantially similar to the first SCR system 150a in structure and function.

In such embodiments, the controller 170 can be further configured to determine the operational parameters of the third portion and the fourth portion of the exhaust gas based upon the operational parameters of the first portion of the exhaust gas, as described herein.

In particular embodiments, a first bank and a second bank of an aftertreatment system, which are configured to have a portion of an exhaust gas flow through each of the banks, can have different lengths. For example, FIG. 2 is a schematic diagram of an aftertreatment system 200 for treating exhaust gas (e.g., a diesel exhaust gas) produced by an engine 20. The aftertreatment system 200 includes a first bank 210a structured to receive a first portion of the exhaust gas, and a second bank 210b structured to receive a second portion of the exhaust gas. The first bank 210 includes a first passageway 212a, a first selective catalytic reduction (SCR) system 250a and a controller 270. The second bank 210b includes a second passageway 212b and a second SCR system 250b.

The engine 20 may comprise an IC engine, for example, a diesel engine, a gasoline engine, a natural gas engine, a positive displacement engine, a rotary engine, or any other suitable engine, which converts a fossil fuel into mechanical energy. The engine 20 can be substantially similar to the engine 10 and therefore, not described in further detail herein.

The first passageway 212a is configured to receive the first portion of the exhaust gas from the engine 20. The first passageway 212a can be formed from any suitable material, for example, metals, alloys, ceramics, plastics, any other suitable material or a combination thereof. The first passageway 212a can have any suitable cross-section, for example, circular, rectangular, square, elliptical, or any other suitable cross-section. The first passageway 212a defines a first length $l_1$.

The second passageway 212b is configured to receive the second portion of the exhaust gas form the engine 20. The second passageway 212b can be formed from the same material and have the same cross-section as the first passageway 212a. The second passageway 212b defines a second length $l_2$. The second length $l_2$ is different from the first length $l_2$, such that $l_2$ is greater than $l_1$. In other words, the second passageway 212b is substantially longer than the first passageway 212a. For example, the second $l_2$ can be more than 10% longer than the first length $l_1$. In other embodiments, the second length $l_2$ can be substantially shorter than the first length $l_1$, for example, more than 10% shorter than the first length $l_1$.

The different lengths of the first passageway 212a and the second passageway 212b can cause the first portion of the exhaust gas and the second portion of the exhaust gas to have different flow rates (e.g., volumetric flow rates), or pressure. For example, the Panhandle formula for gas flow through pipes is:

$$q_h = 2.044 e^{-8} E d^{2.6182} \left( \frac{p_1^2 - p_2^2}{L_m} \right)^{0.5394} \tag{1}$$

where $q_h$ is the volumetric flow rate of the exhaust gas, p is pressure of the exhaust gas, $L_m$ is the length of the passageway, d is internal diameter of the passageway, and E is the flow efficiency factor (0.92). Every other parameter being the same, the flow rate is inversely dependent upon the length of the passageway. The first passageway 212a and the second passageway 212b have about the same cross-section, and are formed from the same material, the only difference being the second passageway 212b has a longer length than the first passageway 212a. From equation 1, it is thus expected that the second portion of the exhaust gas flowing through second passageway 212b will have a smaller flow rate (i.e., volumetric flow rate) than the first portion of the exhaust gas.

The first SCR system 250a is fluidly coupled to the first passageway 212a. The first SCR system 250a is configured to receive the first portion of the exhaust gas and treat the first portion of the exhaust gas. The first SCR system 250a can be substantially similar in structure and function to the first SCR system 150a described with respect to the aftertreatment system 100, and is therefore not described in further detail herein. An injection port 258a is disposed on a sidewall of the first SCR system 250a. The injection port 258a is configured to communicate an exhaust reductant (e.g., a diesel exhaust reductant) into the first SCR system 250a, as described with respect to the aftertreatment system 100.

The second SCR system 250b is fluidly coupled to the second passageway 212b. The second SCR system 250b is configured to receive the second portion of the exhaust gas and treat the second portion of the exhaust gas. The second SCR system 250b can be substantially similar in structure and function to the first SCR system 250a. The second SCR system 250b also includes an injection port 258b disposed on a sidewall of the second SCR system 250b. The injection port 258b is configured to communicate an exhaust reductant into the second SCR system 250b. Moreover, a filter, a body mixer and/or an oxidation catalyst can be fluidly coupled to the first SCR system 250a and the second SCR system 250b, as described with respect to the aftertreatment system 100.

A plurality of sensors are disposed on the first bank 210a of the aftertreatment system 100, and are configured to sense operational parameters of the first portion of the exhaust gas. These include a first NOx sensor 253 disposed on the first passageway 212a proximal to an inlet 252a of the first SCR system 250a. The first NOx sensor 253 is configured to sense a quantity of NOx in the first portion of the exhaust gas before entering the SCR system 250a. A first temperature sensor 255 is disposed on the inlet 252a and configured to sense a temperature of the first portion of the exhaust gas entering the first SCR system 250a.

A second NOx sensor 257 and a second temperature sensor 259 are disposed on an outlet 254a of the first SCR system 250a, and configured to sense a quantity of NOx in the first portion, and a temperature of the first portion of the exhaust gas exiting the first SCR system 250a. Any other sensors can also be included in the plurality of sensors. Such sensors can include, for example, ammonia sensors, and/or oxygen sensors. Moreover, the number of NOx sensors and temperature sensors included in the plurality of sensors disposed on the first bank 210a can also be increased.

The controller 270 is disposed on the first SCR system 250a. In other embodiments, the controller 270 can be disposed at any other location, for example, on the engine 20 or included in an onboard computer, for example, a master controller of a vehicle (e.g., a truck, an excavation equipment, etc.) that includes the engine 20. The controller 270 is configured to determine operational parameters (e.g., NOx quantity and/or temperature before entering and after exiting the first SCR system 250a) of the first portion of the exhaust gas. Furthermore, the controller is also electrically coupled to the injection port 258a of the first SCR system 250a, and the injection port 258b of the second SCR system 250b. The controller 270 can be configured to sense and/or monitor an amount of the exhaust reductant communicated to the first SCR system 250a and the second SCR system 250b by the injection ports 258a and 258b, respectively.

The controller 270 is also configured to determine operational parameters of the second portion of the exhaust gas based upon the operational parameters of the first portion of the exhaust gas. As described herein, the first passageway 212a and the second passageway 212b have different lengths, and thus the first portion and the second portion of the exhaust gas have different flow rates. To account for this, the controller 270 is configured to determine a correction factor from the first length $l_1$ of the first passageway 212a and the second length $l_2$ of the second passageway. The correction factor can be, for example, a ratio of the first length $l_1$ to the second length $l_2$ or any other correction factor. The controller 270 determines the operational parameters of the second portion of the exhaust gas from the operational parameters of the first portion of the exhaust gas using the correction factor.

In other embodiments, the aftertreatment system 200 can include more than two banks, for example, three banks, four banks or even more. Each bank can include passageways configured to receive a portion of the exhaust gas. Furthermore, each passageway can have a length which is different from the length of the first passageway 212a. In such embodiments, the controller 270 can be configured to determine a correction factor for each of the passageways from the length $l_1$ of the first passageway and a length of each of the other passageways. Using each of the correction factors, the controller 270 can be configured to determine the operational parameters of the portions of the exhaust gas flowing through each bank using the correction parameters for each of the multiple passageways.

In some embodiments, a controller (e.g., the controller 170 or 270) and a plurality of sensors (e.g., the plurality of sensors included in the aftertreatment system 100 or 200) can be included in a monitoring system for determining operational parameters of an exhaust gas from an engine flowing through an aftertreatment system (e.g., the aftertreatment system 100 or 200).

The plurality of sensors are disposed on at least one of a first passageway and a first selective catalytic reduction (SCR) system (e.g., the first passageway 112a and/or the first SCR system 150a). The first passageway is configured to receive a first portion of the exhaust gas from the engine (e.g., the engine 10). The first SCR system is fluidly coupled to the first passageway and configured to receive the first portion of the exhaust gas and treat the first portion of the exhaust gas. The plurality of sensors (e.g., the NOx sensors 153 and 159, the temperature sensors 155 and 157, or any other sensors) are configured to sense the operational parameters of the first portion of the exhaust gas.

The controller is in electronic communication with the plurality of sensors. The controller is configured to receive electronic signals from the plurality of sensors and determine operational parameters of the first portion of the exhaust gas (e.g., amount of NOx gas, oxygen, temperature, etc.). Furthermore, the controller is configured to determine operational parameters of the second portion of the exhaust gas from the first operational parameters. The second portion of the exhaust gas flows through a second passageway (e.g., the second passageway 112b) and a second SCR system (e.g., the second SCR system 150b). The second passageway is configured to receive the second portion of the exhaust gas from the engine (e.g., the engine 10). The second SCR system is fluidly coupled to the second passageway and configure to receive and treat the second portion of the exhaust gas.

A flow rate of the first portion of the exhaust gas can be similar to the flow rate of the second portion of the exhaust gas, for example, when the first passageway has a first length about the same or otherwise the same as a second length of the second passageway. In other embodiments, the first passageway (e.g., the first passageway 212a) can have a first length different than a second length of the second passageway (212b). In such embodiments, the controller can be configured to determine a correction factor from the first length and the second length. The controller can then determine the operational parameters of the second portion of the exhaust gas from the operational parameters of the first portion of the exhaust gas using the correction factor.

Figure 3:
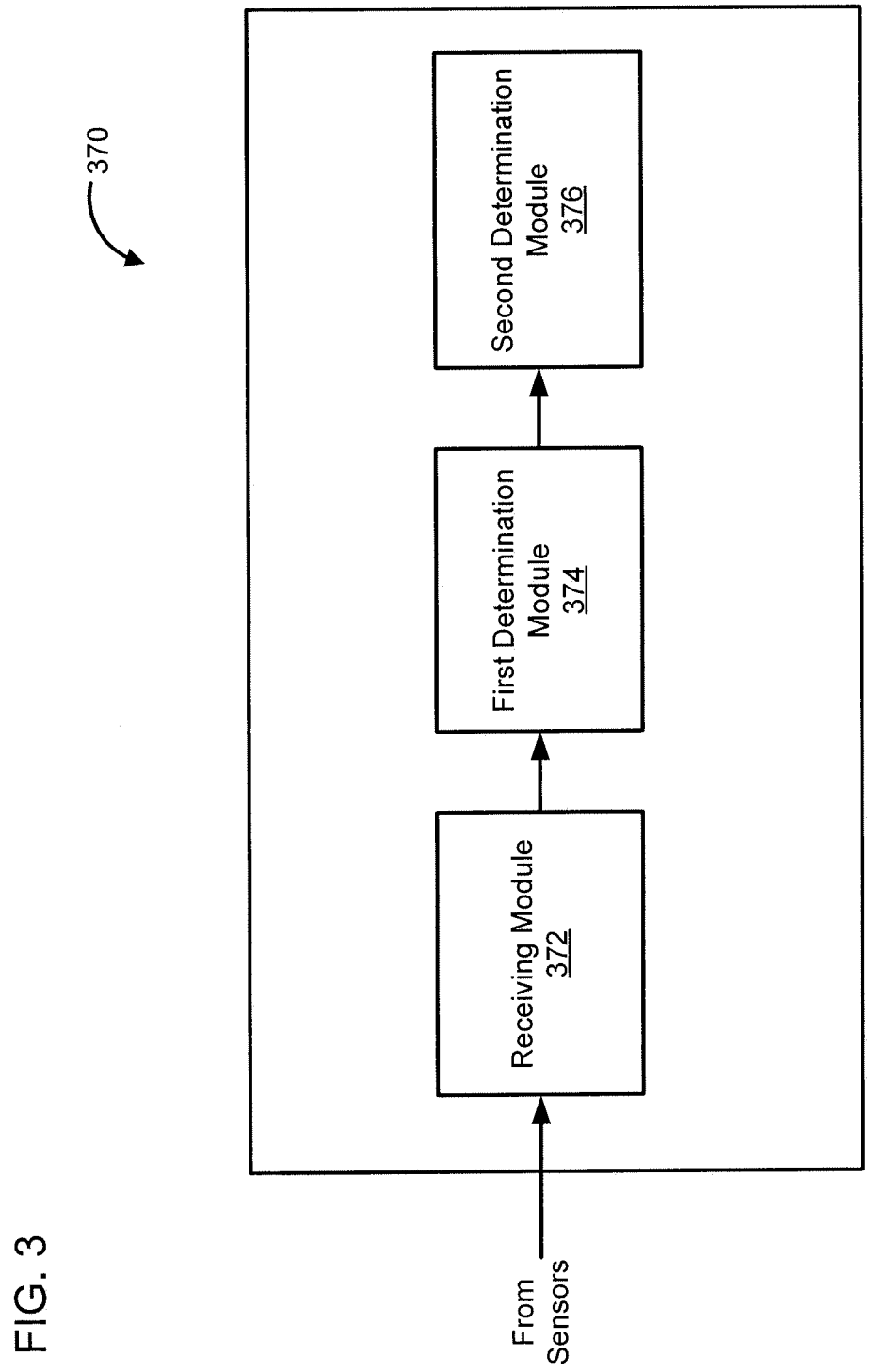
FIG. 3 is a schematic block diagram of a controller module for measuring operational parameters of an exhaust gas, according to one embodiment.

In particular embodiments, a controller module can be used to determine operational parameters of an exhaust gas. FIG. 3 shows a schematic block diagram of a controller module 370 for measuring operational parameters of an exhaust gas. The controller module 370 includes a receiving module 372, a first determination module 374, and a second determination module 376.

The receiving module 372 is configured to receive signals from a plurality of sensors disposed on at least one of a first passageway (e.g., the first passageway 112a or 212a) and a first selective catalytic reduction (SCR) system (e.g., the first SCR system 150a or 250a). The first passageway is configured to receive a first portion of the exhaust gas from an engine (e.g., the engine 10 or 20). The first SCR system is fluidly coupled to the first passageway and configured to receive and treat the first portion of the exhaust gas. The plurality of sensors (e.g., the plurality of sensors included in the aftertreatment system 100 or 200) are configured to sense operational parameters of the first portion of the exhaust gas. The operational parameters can include, for example, an amount of NOx and/or oxygen in the exhaust gas entering and/or exiting the first SCR system, temperature of the exhaust gas at an inlet and an outlet of the SCR system, and/or amount of ammonia in the exhaust gas exiting the SCR system.

The first determination module 374 is electrically coupled to the receiving module 372. The first determination module 374 is configured to process the signals received from the receiving module and determine the operational parameters of the first portion of the exhaust gas. The first determination module 374 can include, for example, a processor (e.g., a microcontroller, a PLC chip, an ASIC chip, etc.) configured to execute instructions for determining the operational parameters of the first portion of the exhaust gas. The instructions can, for example, be stored on a computer readable medium (e.g., a RAM, a ROM, a solid state drive, etc.) included in the controller module 370.

The second determination module 376 is configured to determine the operational parameters of a second portion of the exhaust gas flowing through a second passageway (e.g., the second passageways 112b or 212b) and a second SCR system (e.g., the second SCR system 150b or 250b). The second passageway is configured to receive the second portion of the exhaust gas from the engine. The second SCR system is fluidly coupled to the second passageway and configured to receive and treat the second portion of the exhaust gas.

The second determination module 376 can also include a processor (e.g., a microcontroller, a PLC chip, an ASIC chip, etc.) configured to execute instructions (e.g., stored on a computer readable medium) for determining the operational parameters of the first portion of the exhaust gas. In one embodiment, each of the first determination module 374 and the second determination module 376 can be integrated into a single determination module (e.g., a processor) included in the controller module 370.

In particular embodiments, the first passageway (e.g. the first passageway 150a) can have a first length and the second passageway (e.g., the second passageway 150b) can have a second length which is about the same as the first length. In such embodiments, the operational parameters of the first portion of the exhaust gas is representative of the operational parameters of the second portion of the exhaust gas.

In other embodiments, the first passageway (e.g., the first passageway 250a) can have a first length and the second passageway (e.g., the second passageway 250b) can have a second length which is different than the first length. For example, the second length can be substantially longer than the first length. In such embodiments, the second determination module is configured to determine a correction factor from the first length and the second length. The correction factor can include, for example, a ratio of the first length and the second length. The controller module 370 can then determine the operational parameters of the second portion of the exhaust gas using the correction factor.

As used herein, the terms "about" and "approximately" generally mean plus or minus 10% of the stated value. For example, about 0.5 would include 0.45 and 0.55, about 10 would include 9 to 11, about 1000 would include 900 to 1100.

The terms "coupled," "connected," and the like as used herein mean the joining of two members directly or indirectly to one another. Such joining may be stationary (e.g., permanent) or moveable (e.g., removable or releasable). Such joining may be achieved with the two members or the two members and any additional intermediate members being integrally formed as a single unitary body with one another or with the two members or the two members and any additional intermediate members being attached to one another.

It is important to note that the construction and arrangement of the various exemplary embodiments are illustrative only. Although only a few embodiments have been described in detail in this disclosure, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter described herein. Other substitutions, modifications, changes and omissions may also be made in the design, operating conditions and arrangement of the various exemplary embodiments without departing from the scope of the present invention. Additionally, those of ordinary skill in art will readily appreciate that features of various embodiments described herein may be combined into further embodiments, without departing from the overall scope of the present invention.

What is claimed is:

1. An aftertreatment system, comprising:
 a first passageway configured to receive a first portion of an exhaust gas from an engine;
 a second passageway configured to receive a second portion of the exhaust gas from the engine;
 a first selective catalytic reduction system fluidly coupled to the first passageway, the first selective catalytic reduction system configured to receive the first portion of the exhaust gas and treat the first portion of the exhaust gas;
 a second selective catalytic reduction system fluidly coupled to the second passageway, the second selective catalytic reduction system configured to receive the second portion of the exhaust gas and treat the second portion of the exhaust gas;
a plurality of sensors disposed only on at least one of the first passageway and the first selective catalytic reduction system, the plurality of sensors configured to only sense first operational parameters of the first portion of the exhaust gas; and
a controller in electronic communication with the plurality of sensors, the controller configured to:
determine the first operational parameters of the first portion of the exhaust gas based upon signals received from the plurality of sensors; and
determine second operational parameters of the second portion of the exhaust gas based upon the first operational parameters.

2. The aftertreatment system of claim 1, wherein the plurality of sensors include at least one of a temperature sensor, a NOx sensor, an ammonia sensor, and an oxygen sensor.

3. The aftertreatment system of claim 1, wherein the aftertreatment system includes at least one of a filter, a body mixer, and an oxidation catalyst fluidly coupled to each of the first selective catalytic reduction system and the second catalytic reduction system.

4. The aftertreatment system of claim 1, wherein the first passageway has a first length and the second passageway has a second length, the first length about the same as the second length.

5. The aftertreatment system of claim 4, wherein the first length is the same as the second length.

6. The aftertreatment system of claim 1, wherein the first passageway has a first length and the second passageway has a second length, the first length different from the second length.

7. The aftertreatment system of claim 6, wherein a temperature sensor is disposed in the first passageway, the temperature sensor configured to sense a temperature of the exhaust gas flowing in the first passageway.

8. The aftertreatment system of claim 7, wherein a NOx sensor is disposed in the first passageway, the NOx sensor configured to sense a quantity of NOx gas in the exhaust gas flowing the first passageway.

9. The aftertreatment system of claim 8, wherein the aftertreatment system includes a diesel oxidation catalyst.

10. The aftertreatment system of claim 6, wherein the controller is configured to:
determine a correction factor from the first length and the second length; and
determine the second operational parameters of the second portion of the exhaust gas from the first operational parameters of the first portion of the exhaust gas using the correction factor.

11. The aftertreatment system of claim 1, wherein the engine comprises an off-highway engine.

12. The aftertreatment system of claim 11, wherein the engine comprises a diesel engine.

13. A monitoring system for determining operational parameters of an exhaust gas flowing through an aftertreatment system, the monitoring system comprising:
a plurality of sensors disposed only on at least one of a first passageway and a first selective catalytic reduction system, the first passageway configured to receive a first portion of the exhaust gas from an engine, the first selective catalytic reduction system fluidly coupled to the first passageway and configured to receive the first portion of the exhaust gas and treat the first portion of the exhaust gas, the plurality of sensors configured to only sense first operational parameters of the first portion of the exhaust gas; and
a controller in electronic communication with the plurality of sensors, the controller configured to receive electronic signals from the plurality of sensors and determine the first operational parameters of the first portion of the exhaust gas, the electronic unit further configured to determine second operational parameters of a second portion of the exhaust gas from the first operational parameters, the second portion of the exhaust gas flowing through a second passageway and a second selective catalytic reduction system, the second passageway configured to receive the second portion of the exhaust gas from the engine, the second selective catalytic reduction system fluidly coupled to the second passageway, the second selective catalytic reduction system configured to receive the second portion of the exhaust gas and treat the second portion of the exhaust gas.

14. The monitoring system of claim 13, wherein the plurality of sensors include at least one of a temperature sensor, a NOx sensor, an ammonia sensor, and an oxygen sensor.

15. The monitoring system of claim 13, wherein the first passageway has a first length and the second passageway has a second length, the first length about the same as the second length.

16. The monitoring system of claim 15, wherein the first length is the same as the second length.

17. The monitoring system of claim 13, wherein the first passageway has a first length and the second passageway has a second length, the first length different from the second length.

18. The monitoring system of claim 17, wherein the controller is configured to:
determine a correction factor from the first length and the second length; and
determine the second operational parameters of the second portion of the exhaust gas from the first operational parameters of the first portion of the exhaust gas using the correction factor.

19. The monitoring system of claim 13, wherein the engine includes an off-highway engine.

20. The monitoring system of claim 19, wherein the engine includes a diesel engine.

21. A controller module for determining operational parameters of an exhaust gas, comprising:
a receiving module configured to receive signals from a plurality of sensors disposed only on at least one of a first passageway and a first selective catalytic reduction system, the first passageway configured to receive a first portion of the exhaust gas from an engine, the first selective catalytic reduction system fluidly coupled to the first passageway and configured to receive the first portion of the exhaust gas and treat the first portion of the exhaust gas, the plurality of sensors configured to only sense first operational parameters of the first portion of the exhaust gas;
a first determination module configured to process the signals to determine the first operational parameters of the first portion of the exhaust gas; and
a second determination module configured to determine second operational parameters of a second portion of the exhaust gas from the first operational parameters, the second portion of the exhaust gas flowing through a second passageway and a second selective catalytic reduction system, the second passageway configured to receive the second portion of the exhaust gas from the engine, the second selective catalytic reduction system fluidly coupled to the second passageway, the second selective catalyst reduction system configured to receive the second portion of the exhaust gas and treat the second portion of the exhaust gas.

22. The controller module of claim 21, wherein the first passageway has a first length and the second passageway has a second length, the first length about the same as the second length.

23. The controller module of claim 22, wherein the first length is the same as the second length.

24. The controller module of claim 21, wherein the first passageway has a first length and the second passageway has a second length, the first length different from the second length.

25. The controller module of claim 24, wherein the second determination module is further configured to:
   determine a correction factor from the first length and the second length; and
   determine the second operational parameters of the second portion of the exhaust gas from the first operational parameters of the first portion of the exhaust gas using the correction factor.

* * * * *